(12) United States Patent
Makdissi et al.

(10) Patent No.: US 8,577,327 B2
(45) Date of Patent: Nov. 5, 2013

(54) SYSTEM, METHODS AND APPARATUS FOR WAKING AN AUTONOMOUS ACTIVE IMPLANTABLE MEDICAL DEVICE COMMUNICATING BY PULSES TRANSMITTED THROUGH THE INTERSTITIAL TISSUES OF THE BODY

(75) Inventors: Alaa Makdissi, Paris (FR); Karima Amara, Sceaux (FR); Ashutosh Ghildiyal, Clamart (FR)

(73) Assignee: Sorin CRM S.A.S., Clamart Cedex (FR)

( * ) Notice: Subject to any disclaimer, the term of this patent is extended or adjusted under 35 U.S.C. 154(b) by 85 days.

(21) Appl. No.: 13/276,198

(22) Filed: Oct. 18, 2011

(65) Prior Publication Data
US 2012/0093245 A1 Apr. 19, 2012

(30) Foreign Application Priority Data

Oct. 18, 2010 (FR) .................................... 10 58476

(51) Int. Cl.
*H04B 1/16* (2006.01)
*H04K 3/00* (2006.01)
(52) U.S. Cl.
USPC .......................... 455/343.1; 455/574; 607/60
(58) Field of Classification Search
USPC ................. 455/343.1–343.4, 574; 607/60, 72
See application file for complete search history.

(56) References Cited

U.S. PATENT DOCUMENTS

| | | | |
|---|---|---|---|
| 3,456,134 A | 7/1969 | Ko | |
| 4,987,897 A | 1/1991 | Funke | |
| 5,115,236 A * | 5/1992 | Kohler | 340/12.16 |
| 5,411,535 A | 5/1995 | Fujii et al. | |
| 6,141,588 A | 10/2000 | Cox et al. | |
| 2002/0099423 A1 | 7/2002 | Berg et al. | |
| 2005/0256549 A1 | 11/2005 | Holzer | |
| 2006/0136004 A1 | 6/2006 | Cowan et al. | |
| 2006/0217776 A1 | 9/2006 | White et al. | |

(Continued)

FOREIGN PATENT DOCUMENTS

| | | |
|---|---|---|
| GB | 2 350 302 | 11/2000 |
| WO | WO 2007/047681 A2 | 4/2007 |
| WO | WO 2007/149462 | 12/2007 |
| WO | WO 2010/042066 | 4/2010 |

OTHER PUBLICATIONS

Foreign Search Report (Annexe Au Rapport De Recherche Preliminaire; Ralatif A La Demande De Brevet Francais No. FR 1058476 FA 741899, May 13, 2011.

(Continued)

*Primary Examiner* — Lee Nguyen
(74) *Attorney, Agent, or Firm* — Foley & Lardner LLP

(57) ABSTRACT

An autonomous active medical implantable device, with a power supply and a wake-up circuit that responds to receipt of specific pulses transmitted through the interstitial tissues of the body. A transmitter device (40) generates trains of modulated pulses applied to electrodes (22, 24), and a receiver (50) processes (e.g., filter, amplify and demodulate) pulses collected on electrodes (22', 24'). The receiver circuits (50) are selectively activated from a dormant (sleep) state in which they are not powered by a power source (34), to an operational (active) state in which they are powered and able to process (e.g., filter, amplify and demodulate) the collected pulses. A specific wake-up pulse train, configured in a predetermined characteristic pulse pattern, triggers passive wake-up circuits (66) in the receiver (50) to switch the receiver circuits from the sleep state to the operational state.

26 Claims, 4 Drawing Sheets

(56) References Cited

U.S. PATENT DOCUMENTS

| | | |
|---|---|---|
| 2007/0088397 A1 | 4/2007 | Jacobson |
| 2007/0239229 A1 | 10/2007 | Masoud et al. |
| 2007/0276444 A1 | 11/2007 | Gelbart et al. |
| 2008/0046038 A1* | 2/2008 | Hill et al. .................. 607/60 |
| 2008/0048836 A1 | 2/2008 | Bungartz et al. |
| 2008/0071328 A1 | 3/2008 | Haubrich et al. |
| 2008/0262562 A1 | 10/2008 | Roberts et al. |

OTHER PUBLICATIONS

Foreign Search Report (Annexe Au Rapport De Recherche Preliminaire; Ralatif A La Demande De Brevet Francais No. FR 1057691 FA 741502, Apr. 26, 2011.

* cited by examiner

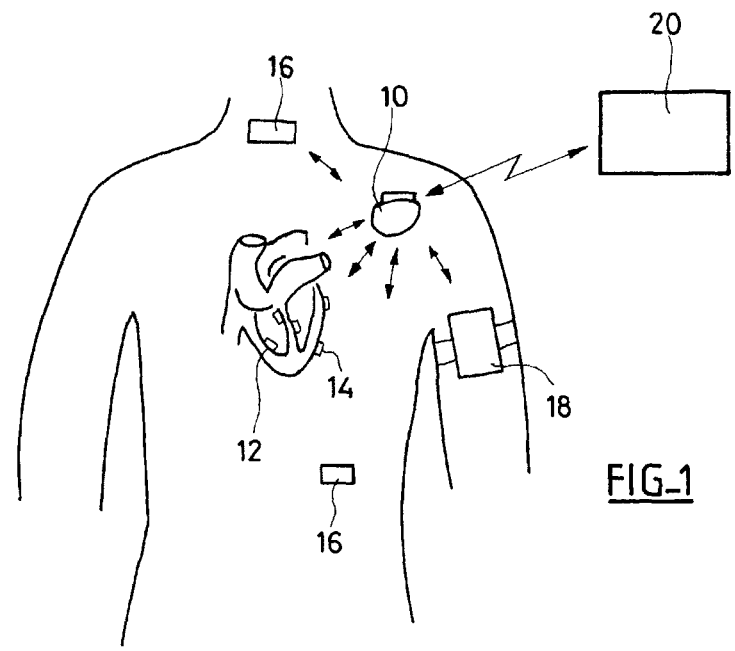
FIG_1
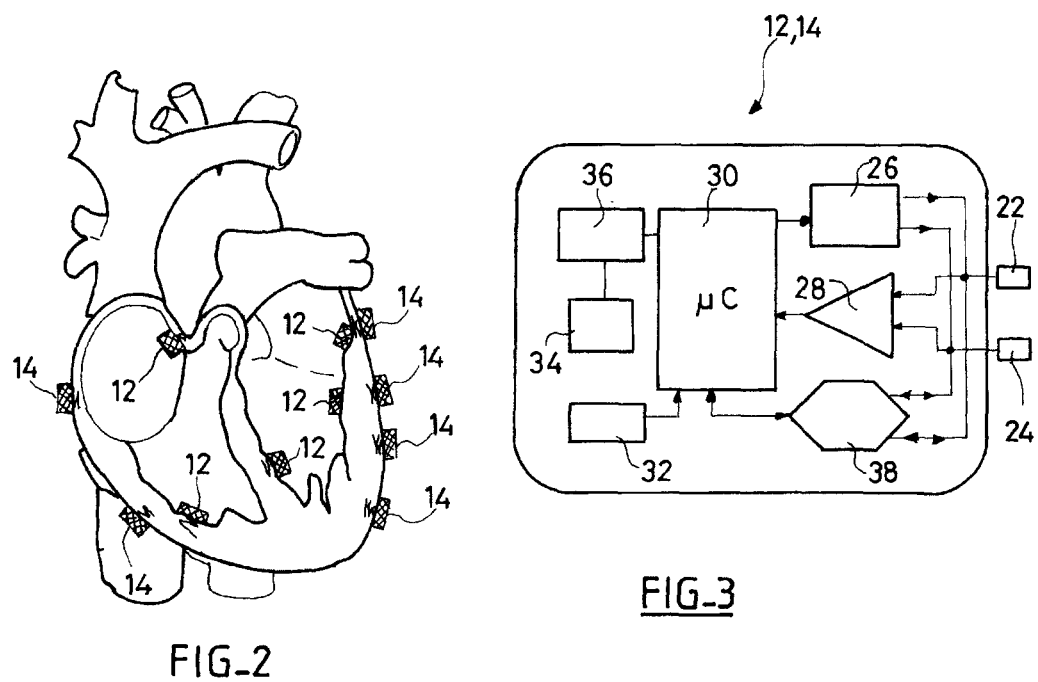
FIG_2
FIG_3

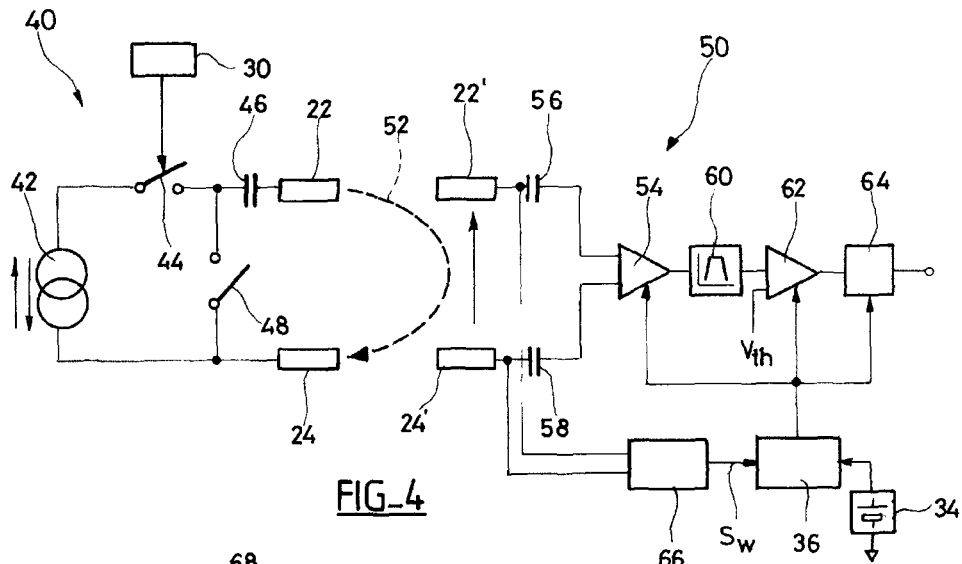
FIG_4
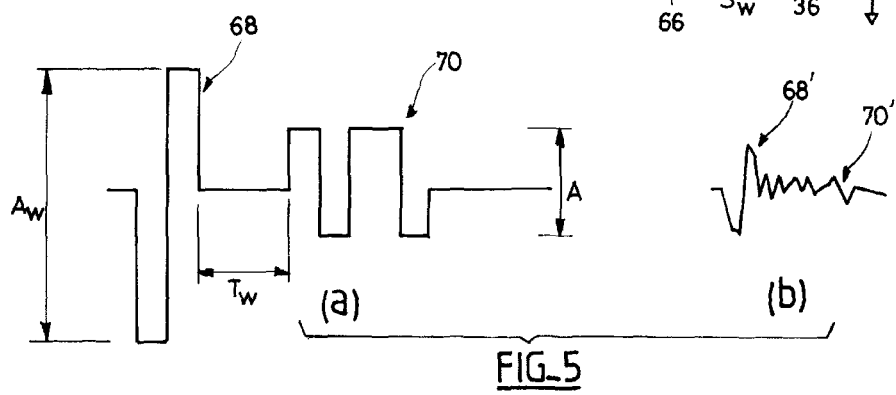
FIG_5
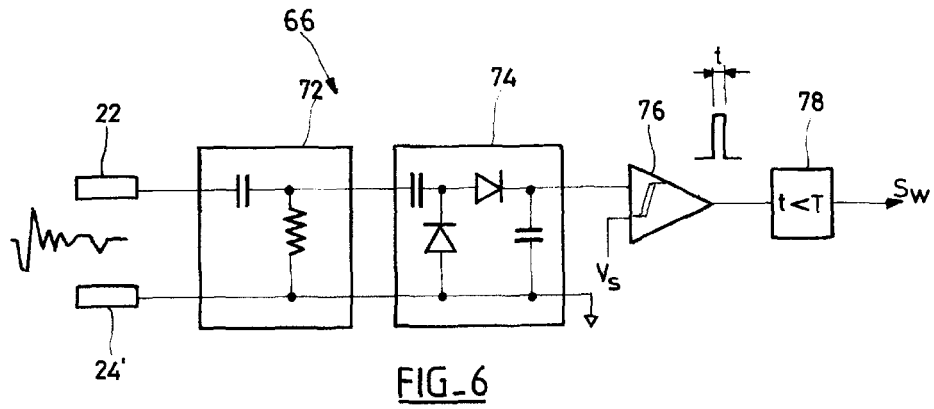
FIG_6

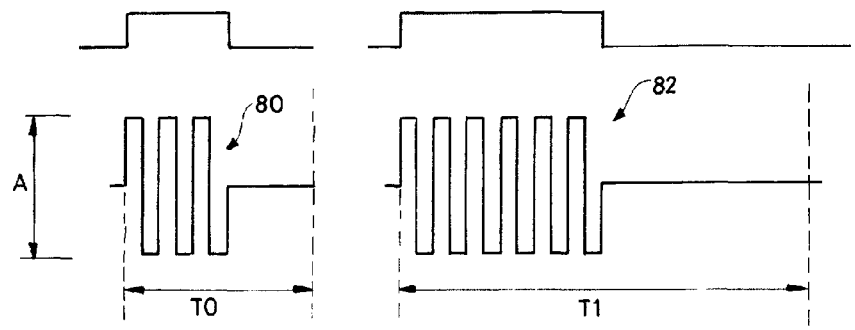
FIG_7
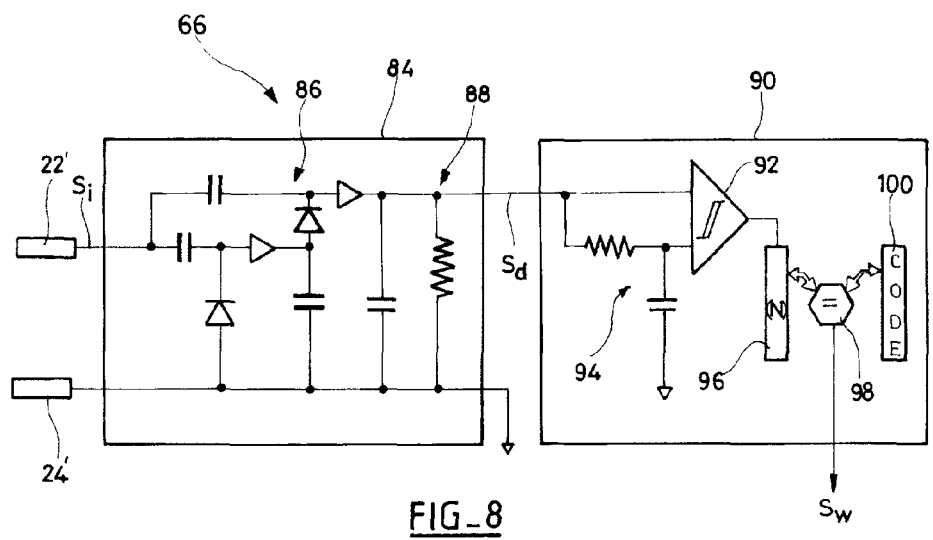
FIG_8

SYSTEM, METHODS AND APPARATUS FOR WAKING AN AUTONOMOUS ACTIVE IMPLANTABLE MEDICAL DEVICE COMMUNICATING BY PULSES TRANSMITTED THROUGH THE INTERSTITIAL TISSUES OF THE BODY

RELATED APPLICATIONS

The present application claims the benefit of French Application No. 10/58476 entitled "Autonomous active medical implant, with a wake-up circuit of the power supply on receipt of pulses transmitted through the interstitial tissues of the body" and filed Oct. 18, 2010, which is hereby incorporated by reference in its entirety.

FIELD OF THE INVENTION

The present invention relates to "medical devices" as defined by the 14 Jun. 1993 Directive 93/42/EEC of the Council of the European Communities, including the "active implantable medical devices" as defined by the 20 Jun. 1990 Directive 90/385/EEC of the Council of the European Communities, more particularly, to devices that continuously monitor a patient's cardiac rhythm and deliver if necessary to the patient's heart electrical pulses for stimulation, resynchronization, cardioversion and/or defibrillation in response to a cardiac rhythm disorder detected by the device, and to neurological devices, cochlear implants, etc., as well as devices for pH measurement or devices for intracorporeal impedance measurement (such as the measure of the transpulmonary impedance or of the intracardiac impedance). The present invention is even more particularly directed to those implantable devices that are autonomous capsules free from any physical connection to a main implanted device (such as the can of a stimulation pulse generator) or a main not-implanted device (e.g., an external device such as a programmer or other device for remote monitoring of the patient), which capsules are considered to be a "remote device" relative to a "main" device, and communicate with the main device or another remote device by intracorporeal communication of signals via the interstitial tissues of the body, which is called human body communication ("HBC").

BACKGROUND

Autonomous implanted capsules are often called "leadless capsules" and distinguished from those electrodes or sensors placed at the distal end of a lead, which lead is traversed throughout its length by one or more conductors, connecting by galvanic conduction, the electrode or sensor to a generator connected at the opposite, proximal end, of the lead. Such leadless capsules are, for example, described in U.S. Patent Publication No. 2007/0088397 A1 and WO 2007/047681 A2 (Nanostim, Inc.) or in the U.S. Patent Production No. 2006/0136004 A1 (EBR Systems, Inc.).

Leadless capsules may be epicardial capsules fixed to the outer wall of the heart, or endocardial capsules fixed to the inside wall of a ventricular or atrial cavity. Their attachment to the heart wall is usually achieved by a protruding anchor such as a helical screw axially extending from the body of the capsule and designed to screw into and penetrate the heart tissue at the implantation site.

Leadless capsules typically include detection and/or stimulation circuitry to collect depolarization potentials of the myocardium and/or to apply stimulation pulses to the site where the leadless capsule is anchored, respectively. Such leadless capsules include an appropriate electrode, which optionally can be included in an active part of an anchoring screw. It can also incorporate one or more sensors for locally measuring the value of a parameter that is characteristic of the patient's physiological or physical condition, such as, for example, the patient's oxygen level in the blood, endocardial cardiac pressure, heart wall acceleration, and acceleration of the patient as an indicator of physical activity.

It should be understood, however, that the present invention is not limited to a particular type of leadless capsule, and is equally applicable to any type of leadless capsule, regardless of its functional purpose.

Of course, for a leadless capsule to exchange data with a remote device (i.e., in this context a device that is "remote" to the leadless capsule), the leadless capsule incorporates transmitter/receiver means for unidirectional and/or bidirectional wireless communications, as deemed appropriate for the purpose of the leadless capsule. Several techniques have been proposed for such wireless communications, in particular to allow a remote device to centralize the information collected by the leadless capsule and send, if necessary, appropriate instruction controls signals to the leadless capsule. As noted, the remote device in this instance may be an implanted pacemaker, defibrillator or resynchronizer, a subcutaneous defibrillator, or a long-term event recorder, and may be implanted or not implanted, and may be called a main device.

Thus, U.S. Patent Publication No. 2006/0136004 A1 proposes to transmit data by acoustic waves propagating inside the body. This technique is safe and effective, but it nevertheless has the disadvantage of requiring a relatively high transmission power, given the attenuation of acoustic waves into the body, and allows only relatively low data transmission rates.

U.S. Pat. No. 5,411,535 proposes a communication technique based on the use of radiofrequency (RF) waves. This also requires relatively high transmission power, and the attenuation of these waves by intracorporeal tissue is a major barrier to their spread.

Another technique proposed by U.S. Pat. No. 4,987,897 is a data exchange with a remote external device (programmer), through the skin, rather than only an intracorporeal transmission. This transmission is over a relatively short distance, between on the one hand, the housing of a pacemaker implanted in a subcutaneous pocket and, on the other hand, an external programmer placed against the skin near the generator. Currents therefore circulate through the skin in an area very distant from the sensitive areas, particularly in an area very distant from the myocardium, which avoids any risk of disruption of the natural or stimulated depolarization waves of the myocardium.

U.S. Patent Publication No. 2007/0088397 A1 proposes to use the stimulation pulses produced by a leadless capsule as a vehicle for the transmission of data previously collected or created by the leadless capsule. To this purpose, the pulse, instead of presenting a monotonic variation of voltage, is interrupted in a controlled manner for very short durations in order to create in the profile of the pulse very narrow pulses whose sequence corresponds to binary encoding of the information to be transmitted.

Whatever the communication technique used, the processing of the HBC signal collected at the leadless capsule requires significant energy compared to the energy resources available in the leadless capsule. Given its autonomous nature, the leadless capsule can in fact only use its own power resources, such as an energy harvester circuit (based on the movement of the leadless capsule) and/or a small integrated battery. The management of the available energy is thus a crucial point for the development of HBC techniques with and between autonomous leadless capsules.

It is recognized that the communication between a leadless capsule and a remote device is not continuous, and the active circuitry for signal processing (e.g., one or more of signal conditioning, amplification, scanning, filtering, decoding, and signal analysis) is therefore unnecessarily powered, with a negative impact on the autonomy of the leadless capsule and hence its useful lifetime, in the absence of a specific sleep implementation. By a "sleep implementation" it is meant that the relevant active circuits are powered down or off to conserve energy consumption (generally referred to as "sleep" or a "sleep mode").

On the other hand, if the active circuits of the receiver are in a sleep mode then it becomes impossible to detect the occurrence of a HBC signal.

There is thus a need to "wake-up" the leadless capsules from a sleep mode when needed, with a relatively low latency to avoid burdening the flow of HBC signals or the responsiveness of the leadless capsule to the control signals that it receives by this HBC technique.

One known wake-up technique is to keep the active receiver circuits in a sleep implementation and wake them up at regular intervals to detect the presence of signals sent by another leadless capsule or another remote device. This technique requires a compromise between a low frequency of wake-ups—which saves energy but reduces the responsiveness—and conversely a higher frequency—which improves responsiveness but only slightly reduces the average energy consumption of the capsule in the long term.

US Patent Publication No. 2008/071328 A1 proposes an implantable leadless device equipped with a wake-up circuit activated by RF or acoustic signals (thus, not HBC signals) emitted from another remote device, these signals being possibly coded according, for example, to a particular addressing scheme allowing the wake-up of only one particular (or more) selected device. The use of non-HBC signals for the wake-up, however, requires the implantation of specific communication circuits both on the receiver and on the transmitter side of the communication.

The present invention, however, provides a different approach. It is based primarily on the use of a clock circuit that is a passive receiver (that is to say, a wake-up circuit that operates without an amplifier or any other circuit component having a significant energy consumption as compared to the overall energy balance of the leadless capsule) constantly able to detect the reception of a HBC signal. Only when such an HBC signal has been detected, does the clock circuit wake-up the system receiver circuit and activate the amplifiers and the other active circuits that need energy.

One of the major difficulties of this approach has been the low amplitude level of HBC signals to be detected by the wake-up circuit, given the rapid attenuation of propagating electrical pulses in the interstitial tissues of the body.

Another difficulty is that, the pulses of HBC signals can be mixed with parasitic electrical signals of relatively high level, such as the body's natural myopotentials and the cardiac depolarization waves propagating within the myocardium—hence there is a deteriorated signal/noise ratio. The stimulation pulses delivered by an implanted generator should also be discriminated so as to exclude them, which stimulation pulses are locally applied at specific sites of the myocardium, but then diffuse around the site of stimulation in a large area before being substantially attenuated.

It is desirable that the implemented technique should be able to address these issues and ensure effective screening and discrimination of all spurious signals.

As regards more particularly the signal attenuation by body tissues in the frequency range 500 kHz-10 MHz (band B), which is the one with minimal attenuation by the interstitial tissues of the body, the attenuation in this frequency range typically varies between 10 dB and 40 dB, depending on the distance between the transmitter and the receiver, the distance between the respective electrodes of the pair of electrodes of the transmitter or of the receiver, and the surface of these electrodes. A typical attenuation value is 20 dB at 1 MHz for a distance of 10 to 12 cm between the transmitter and the receiver.

But in extreme conditions, this attenuation can reach 60 dB, so that the clock signal sent to the leadless capsule is mixed in a background noise, thus having both a very low pulse amplitude to be detected and a very poor signal/noise ratio.

OBJECT AND SUMMARY OF THE INVENTION

It is, therefore, an object of the present invention to preserve the useful life of a leadless capsule, dependent on an integrated self-powered system. It is another object to provide a leadless capsule that is not likely to be affected by spurious electrical signals present in the body tissues, including the disruption by cardiac myopotentials and other potentials present in the body, or by the stimulation pulses that may be delivered by an implanted device. It is yet another object of the present invention to have a leadless capsule that does not require complex circuits for a sleep implementation and has minimal latency in response to a wake-up pulse, to ensure a high responsiveness of the leadless capsule.

One embodiment of the present invention is directed to a system of the general type disclosed in US Patent Publication No. 2008/071328 A1 cited above, namely, including at least two active implantable medical devices that communicate with each other intracorporeally by electrical signals consisting of electrical pulses conducted by the interstitial tissues of the body (HBC signals). The system includes at least one device acting as a transmitter device and at least one device acting as a receiver device, each device being remote from the other. The transmitter device comprises a transmitter that generates modulated pulse trains having a series of HBC signal pulses that are applied to electrodes of the transmitter device. The transmitter, prior to or at the start of a communication sequence with the receiver device, also generates a specific wake-up signal, configured according to a predetermined characteristic pattern. The wake-up signal may or may not be modulated by the transmitter device along with the pulse train of information being communicated to the receiver device. The receiver device includes electrode terminals to receive the HBC signals and receiver circuits that process, e.g., condition, filter, amplify and demodulate signal pulse trains, the HSC signals collected at the receiver device electrode terminals. These receiver circuits are selectively activated from a sleep implementation, wherein they are not powered by a power source of the receiver device, to an operational or awake state, wherein they are powered for, e.g., filtering, amplifying and demodulating the collected pulses.

The receiver device thus includes, in addition to the receiver circuits, a clock circuit (also referred to herein as a "wake-up circuit") that discriminates the reception of a specific wake-up signal, as corresponding to the predetermined characteristic pattern of the specific wake-up signal emitted by the transmitter and, in response, switches the receiver circuits from the sleep state to the active or operational state.

In one embodiment, the wireless communication is an intracorporeal communication of HBC signals constituted by said electrical pulses, conducted by the interstitial tissues of the body; the said specific wake-up signal generated by said transmitter is a train of said pulses configured according to a predetermined characteristic pulse pattern; and the clock circuit means includes detector means and an hysteresis comparator.

In one preferred embodiment, the wake-up circuit is advantageously devoid of an amplifier circuit, and may in particular comprise a hysteresis comparator. The permanent energy consumption of the wake-up circuit is typically less than 10 nW.

In one embodiment, the pulses of the specific wake-up pulse train are preferably biphasic pulses, each including positive and negative alternations.

In a first embodiment of the invention, the transmitter generates the predetermined characteristic pattern in the form of an initial pulse of high amplitude for the wake-up signal, and then generates a following succession of pulses of lower amplitude for communication of desired information to the receiver device. The characteristic pattern may include a period between the initial pulse of high amplitude and the succession of pulses of lower amplitude, selected to set the wakeup latency of the receiver device.

In one embodiment, the wake-up circuit preferably comprises an up-stream high-pass filter for mitigation of parasitic physiological signals present in the interstitial tissues of the body, a detector circuit that is preferably either a peak level detector or a peak-to-peak detector, of the received pulses, and means for inhibiting the switching of the receiver circuits from the sleep state to the operational state upon detection of a received pulse having a width greater than a predetermined upper limit.

In one embodiment of the invention, the transmitter generates the predetermined characteristic pattern of the wake-up signal in the form of a specific sequence of uniform amplitude pulses encoding a predetermined binary code forming a wake-up code. The wake-up circuit include circuits to identify the received pulses, to decode the binary value encoded by these received pulses, and compare the decoded value with a predetermined value stored in the receiver device to determine whether the decoded signal correspond to a specific wake-up signal.

In one preferred implementation of the invention, the transmitter means generates the specific sequence of pulses in the form of a plurality of distinct bursts of pulses, some of these bursts being composed of a first number of pulses encoding a binary '1' and the bursts being made of a second number of pulses, different from the first number, for example, double, encoding a binary '0'. The wake-up circuit then preferably includes an envelope detector delivering as an output a series of binary values each obtained by integration of a received corresponding burst of pulses, and digital circuitry for comparing the detected series of bits to the predetermined stored value. The envelope detector may advantageously include a voltage multiplier circuit.

Another aspect of the present invention is directed to a receiver device for an autonomous active implantable medical device that has wireless communications with a remote active medical device, wherein the receiver device includes an energy source, at least one active circuit element used in connection with the processing of received signals, a pair of electrodes, and a receiver means for collecting a signal at said pair of electrodes and processing said received signal to identify therein a received modulated pulse train. The receiver means includes means for processing the received signal, more specifically demodulating a received modulated pulse train into a received pulse train and identifying in said received pulse train a plurality of pulses corresponding to information being transmitted. The wake-up signal is preferably a biphasic pulse, and the modulated pulse train is preferably a biphasic pulse train, each biphasic pulse having a positive alternation and a negative alternation. The receiver means also includes circuit means for selectively switching the at least one active circuit element between a sleep state not powered by the energy source and an operational state powered for processing the collected signal using said at least one active circuit element. The receiver device also includes a wake-up circuit means for discriminating said received signal and identifying therein a first signal having a predetermined characteristic pulse pattern corresponding to a wake-up signal, and in response, switching the receiver means from the sleep state to the operational state. The wake-up circuit means further comprises a detector circuit, which may be one of a peak level detector and a peak-to-peak detector, and a hysteresis comparator. More preferably, the wake-up circuit means has a permanent energy consumption of less than 10 nW. In an embodiment where the wake-up signal is modulated with the information pulse train, the receiver device first demodulates the received signal and then discriminates the wake-up signal.

Preferably, the wake-up circuit means has no active amplifier circuit.

In one embodiment of the receiver, the predetermined characteristic pattern is an initial pulse having a high amplitude corresponding to the wake-up signal, wherein the following succession of pulses have lower amplitude. The predetermined characteristic pattern also may have a latency period between the initial pulse and the following succession of pulses. Preferably, the wake-up circuit means further comprises means for inhibiting the switching of the receiver means from the sleep state to the operational state upon detection of a received pulse having a width that is greater than an upper predetermined limit (T). In one embodiment, the predetermined value corresponding to an authorized wake-up signal may be a first specific sequence of pulses of relatively uniform amplitude (A) encoding a predetermined binary value forming a wake-up code, and the wake-up circuit means comprises means for indentifying the received signal and decoding therefrom the first signal as a binary value encoded by said received signal first specific sequences of pulses, and comparing said decoded binary value with said predetermined value. Further, the first specific sequence of pulses may be a plurality of distinct bursts of pulses, some of said bursts being a first number of pulses encoding a '1' bit and the other bursts being a second number of pulses, different from the first number, encoding a '0' bit. More preferably, the second number of pulses is double the first number of pulses. Also, the receiver means preferably includes an envelope detector delivering as output a series of binary values each obtained by integration of a received corresponding burst of pulses, and means for comparing said series of bits to said predetermined value. The envelope detector is preferably a voltage multiplier circuit.

Another aspect of the invention is directed towards a transmitter circuit for an active medical device having wireless communication with a remote active medical device, wherein the transmitter device includes a first pair of electrodes and a transmitter circuit that generates a wake-up signal and a following modulated pulse train having a plurality of pulses in a series, the latter corresponding to a communication of desired information to said remote device. The wake-up signal is provided with a predetermined characteristic pulse pattern and optionally may be modulated along with the plurality of pulses corresponding to the information. The generated wake-up signal and modulated pulse train pulses are applied to the electrodes for communication to a remote device. Preferably, the predetermined characteristic pattern has an initial pulse having a high amplitude corresponding to the wake-up signal, and the following succession of pulses have a lower amplitude. The wireless communication is preferably an intracorporeal communication of electrical pulses conducted by the interstitial tissues of a patient's body.

In one embodiment of the transmitter device, the wake-up signal is a biphasic pulse and the modulated pulse train is a biphasic pulse train, with each biphasic pulse having a positive alternation and a negative alternation.

In one embodiment of the transmitter device, the predetermined characteristic pattern includes a latency period ($T_w$) that extends between the initial pulse and the following succession of pulses. Preferably, the predetermined characteristic pattern further comprises a first specific sequence of pulses of uniform amplitude encoding a predetermined binary value forming a wake-up code. The wake-up code can be used by the remote device for authenticating a received signal as a wake-up signal, as discussed herein.

In one embodiment of the transmitter device, the first specific sequence of pulses is a plurality of distinct bursts of pulses, some of said bursts being a first number of pulses encoding a '1' bit and the other bursts being a second number of pulses, different from the first number, encoding a '0' bit. More preferably, the second number of pulses is double the first number of pulses.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which:

FIG. 1 schematically illustrates a representative system of medical devices including leadless capsules, implanted within the body of a patient;

FIG. 2 schematically illustrates a plurality of leadless capsules implanted on the inner and outer walls of a patient's myocardium;

FIG. 3 is a functional block schematic diagram showing the different circuit stages constituting a leadless capsule;

FIG. 4 is a schematic circuit diagram of a transmitter circuit and a receiver circuit in accordance with a preferred embodiment of the present invention;

FIGS. 5a and 5b are timing diagrams showing the shape of a wake-up pulse train according to a first embodiment of the present invention, respectively, as emitted and as received;

FIG. 6 is a schematic circuit diagram of the different circuit stages of a clock circuit according to an embodiment of the present invention, this circuit being able to detect and analyze a pulse such as that in FIG. 5b;

FIG. 7 illustrates the shape of two wake-up pulses emitted according to a second embodiment of the present invention;

FIG. 8 is a schematic circuit diagram of the circuit stages of a wake-up circuit according to the second embodiment of the present invention, circuit being able to detect and analyze the received pulses at the receiver side of FIG. 7.

DETAILED DESCRIPTION OF THE INVENTION

Figure 9:
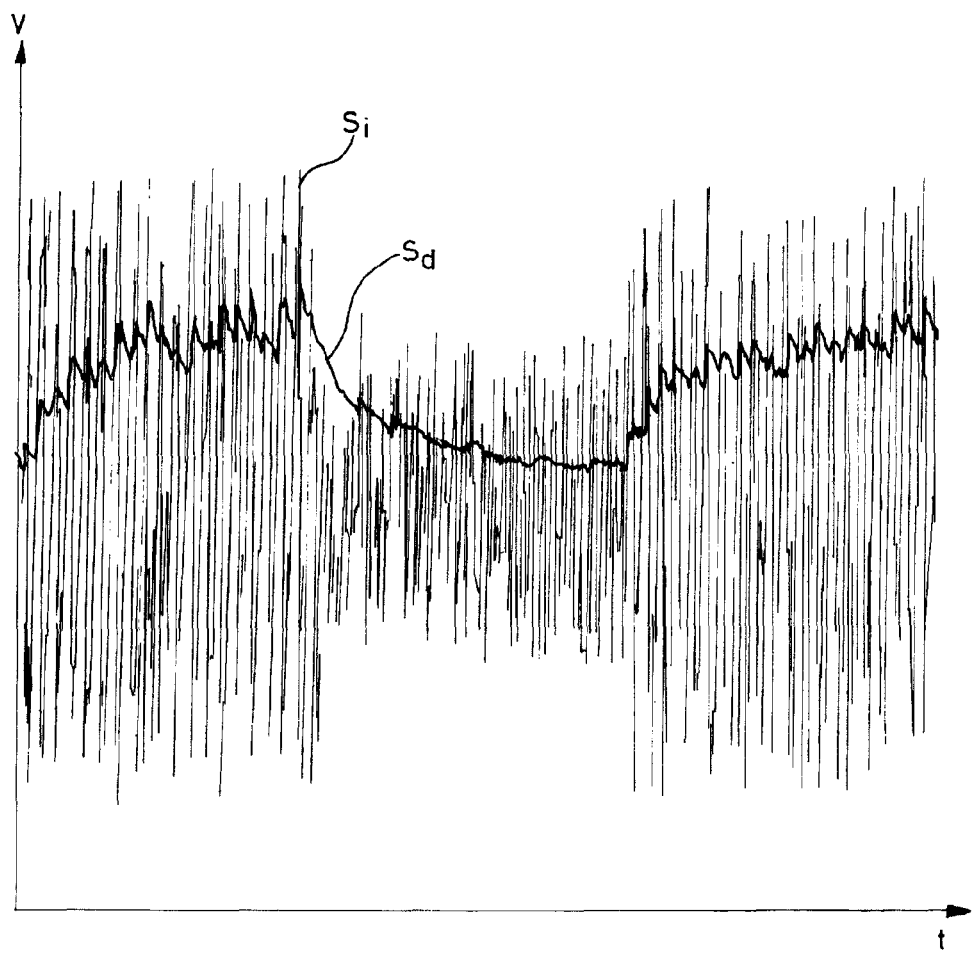
FIG. 9 illustrates, on the same timing diagram, a representative raw wake-up signal, as received, and the corresponding demodulated signal obtained at the output of the envelope detector circuit of FIG. 8.

With reference to the drawings FIGS. 1-9, preferred embodiments of a system, transmitter and receiver, in accordance with the invention will now be described.

In FIG. 1, a system of medical devices 10, 12, 14, 16 implanted within the body of a patient, wirelessly communicating with each other through HBC signals, is illustrated.

Device 10 which may be, for example, a defibrillator/pacemaker/resynchronizer, or a subcutaneous defibrillator or a long-term event recorder, is implanted in the patient and considered to be a "master" device of a network comprising a plurality of "slave" devices 12 to 18 with which it is capable of communicating by HBC signals. These slave devices may include intracardiac 12 or epicardial 14 leadless capsules implanted directly onto the patient's heart, other devices 16 such as myopotential sensors or neurological stimulation devices implanted at suitable locations, and possibly an external device 18, e.g., disposed on an armband and provided with electrodes in contact with patient's skin.

Device 10 can also be used as a gateway to the outside world to communicate with an external (not implanted) device 20 such as a programmer or a remote data transmission device, with which device 10 can communicate via RF telemetry in the MICS (Medical Implants Communication System) band 402-405 MHz, or the unmarked public ISM (Industrial, Scientific and Medical) bands 863-870 MHz, 902-928 MHz and 2.4 GHz, or such other frequency band as may used by medical devices.

Each of the devices 10 to 18 is provided with at least one pair of electrodes which are in direct contact with the tissues of the body (implanted devices 10, 12, 14, 16), or in contact with the skin (external device 18).

With reference to FIG. 2, an example of a leadless capsule implanted either on the anterior part of the myocardium, within an atrial or ventricular cavity (endocardial capsules 12) or on an outer wall of the same myocardial (epicardial capsules 14) is shown. These capsules, which are described for example in U.S. Patent Publication No. 2007/0088397 A1, WO 2007/047681 A2 and U.S. Patent Publication No. 2006/0136004 A1 above, which disclosures are hereby incorporated herein by reference, are attached to the heart wall using a projecting anchoring screw for penetrating into the cardiac tissue by screwing at the implant site. The screw can either be a passive screw, serving only for fixing the capsule, or an active screw, for collecting the signals of depolarization that propagate in the myocardium tissue and/or for delivering localized stimulation pulses to the implantation site.

FIG. 3 schematically shows the different internal circuits of leadless capsules 12, 14 (and, mutatis mutandis, of the other implanted devices designed to communicate with each other via HBC signals in accordance with the present invention). Each leadless capsule contains a pair of electrodes 22, 24, one of which may also be constituted by the anchoring screw in the heart tissue. These electrodes are connected to a stimulation pulse generator circuit 26 (for an active leadless capsule incorporating this function) and/or a detection circuit 28 for the collection of depolarization potentials collected between the electrodes 22 and 24.

A central processing unit circuit 30 is a microprocessor and/or microcontroller based device executing suitable software instructions (CPU) that provides control of the various functions of the leadless capsules, including delivery of stimulation pulse (if applicable), and memorization (storage in memory) of all or selected collected signals. The leadless capsule can also be equipped with a sensor 32 such as, for example, an acceleration sensor, a pressure sensor, a hemodynamic sensor, a temperature sensor, an oxygen saturation sensor for obtaining a relevant parameter of the patient. The leadless capsule is preferably powered by souce 34, which may be a small battery or by an energy harvester circuit (or both) supplying all the powered circuits via a power management stage 36.

The electrodes 22 and 24 are also connected to a modulator/demodulator circuit 38 coupled to the CPU 30 for emitting and/or receiving pulses used for wireless HBC signals. Thus, depending on whether the stimulation (module 26) and collection (module 28) circuits are present or not, the electrodes 22, 24 can provide a single, double or triple function, namely, stimulation and/or collection of cardiac potentials (if applicable) and/or transmission of information obtained by the sensor 32 (if necessary) and emission/reception for the HBC signals (in any case).

The present invention improves the power management stage 36, including the circuits and methods used to selectively power the active consumer-of-energy circuits (e.g., amplifier 28, CPU 30, HBC transmission/reception circuit 38), only when they are needed. The rest of the time, these active circuits are put to sleep, so they do not consume any power or any significant amount of power.

Power management stage 36 thus includes clock circuitry for this wake-up function consisting only of passive components and/or components with very low power consumption (so as to be equivalent to passive components in terms of total energy balance), as described in detail hereafter.

The wake-up circuit has the function of detecting, during the sleep of the receiver circuits (i.e., the active circuits), pulse trains configured in a predetermined characteristic pattern specific to trigger a wake-up of those active circuits in a sleep mode.

The pulse train that constitute the wake-up signal is remotely generated by one device such as a leadless capsule that has a pacemaker function or a subcutaneous device for monitoring cardiac activity and generating stimulation, resynchronization and/or defibrillation pulses, or by another leadless capsule of the system. The remote device can, for example, provide the function of a master device (e.g., a hub in a star wireless network system architecture), with the other various leadless capsules in the system being slave devices for receiving a communication in this one direction from the master device—it being understood that for communication in the opposite direction, the roles are reversed).

FIG. 4 schematically illustrates the elements used by the master device (or "transmitter device") and by the slave leadless capsule to be woken up (or "receiver device") in accordance with a preferred embodiment of the present invention.

The circuits of the transmitter device 40 includes a current source (or voltage source) 42, adjustable by command to generate a voltage pulse of an appropriate value. The CPU 30 controls the opening and closing of switches, including the closure of a switch 44 to inject the current in a predetermined direction and for a predetermined time interval. The injected current 52 flows (via a coupling capacitor 46, shared or not with the stimulation stage, to avoid sending any direct voltage on the electrodes) through the patient's body from one of the electrodes 22 up to the other electrode 24. Switch 48 can then be operated to discharge capacitor 46 of any residual charge due to the compensation errors of the positive and negative pulses. After injecting a first alternation, the procedure is the same to inject the next alternation by reversing the direction of the current, so as to obtain biphasic pulses, as described below.

Preferably, biphasic pulses are generated to minimize the injected residual charge into the patient's heart and also reduce the possible corrosion of materials. In the examples shown, these biphasic pulses are delivered in the form of two successive, positive and negative (or vice versa), alternations, with a square and symmetrical shape (i.e., the same magnitude in absolute terms for the same two oscillations period). Other waveforms are possible, however, and the examples set forth here should be considered as not limiting.

Referring to FIG. 4, reference 50 designates a receiver circuit of the receiver device: current 52 circulating through the body generates between the electrodes 22' and 24' of the receiver a potential difference that is applied to an amplifier stage 54 via the connecting capacitors 56 and 58 to eliminate any DC bias. The resulting amplified signal is applied to a bandpass filter 60 to filter the parasitic signals outside the relevant band, and the resulting filtered signal is applied to a threshold comparator 62, along with a reference $V_{th}$, and to a demodulator stage 64.

In accordance with one embodiment of the invention, circuits 54, 62 and 64, are active circuits (energy consumers) of the receiver device and, preferably together with any other active circuits, are powered only when necessary to reduce the average energy consumption of the receiver device.

In accordance with the present invention, electrodes 22' and 24' are connected to a clock (wake-up) circuit 66 for detecting and discriminating the arrival of specific wake-up pulses on these electrodes. Wake-up circuit 66 responds to such a wake-up pulse train by delivering a control wake-up signal $S_w$ that is applied to the input of power management stage 36 to supply the active circuits 54, 62, 64, previously in a sleep state, with the appropriate voltage from power source 34.

Two specific embodiments of the present invention will now be described, that are specifically adapted to different qualities of the communication channel between a given transmitter device and a given receiver device, namely: (i) the signal attenuation between the transmitter and the receiver, and (ii) the signal/noise ratio more or less degraded by interfering signals present in the interstitial tissues.

The first embodiment, illustrated in FIGS. 5 and 6, is optimized for communication channels with low attenuation and a good signal/noise ratio. "Low attenuation" should be understood to mean an attenuation between ×10 and ×100, or between 20 to 40 dB. In this case, a predetermined characteristic pulse pattern, such as that shown in FIG. 5a, including a (biphasic) pulse 68 of high amplitude $A_w$, is generated, forming a wake-up signal that is used to trigger the wake-up, followed by a succession of (also biphasic) pulses 70 of smaller amplitude A, for the HBC signals to be delivered to the receiver device.

A biphasic pulse of ±1.5 V (i.e., a peak-to-peak amplitude $A_w$=3 V) can for example be generated at the transmitter device side, which provides for an attenuation of between 20 and 40 dB, and a pulse having an amplitude between about ±150 mV and ±15 mV, at the receiver device side.

The received signal corresponding to the transmitted signal is comparable to that illustrated in FIG. 5b, which is an attenuated and filtered (by the tissues of the body) representative version of the original emitted signal. The received signal is thus a pulse train having a first pulse 68' of relatively higher amplitude and a series of pulses 70' of lower amplitude which follow.

With reference to FIG. 6 the different stages of the wake-up circuit 66 are shown. Circuit 66 includes a high pass filter 72 receiving the upstream signal collected on the electrodes 22' and 24' and delivering as an output the filtered signal to a detector stage 74. Detector stage 74, which can be a simple amplitude detector or, more preferably, a peak-to-peak detector such as that illustrated in FIG. 6. Using a peak-to-peak detector improves the sensitivity of the detection system. The output of detector 66 is applied to the input of a hysteresis comparator 76, which switching generates the signal $S_w$, intended to awake the active circuits of the receiver device.

High pass filter 72 allows filtering the physiological signals so as not to make them visible to the detector and comparator circuits arranged upstream, and thus avoid false wake-ups. Filter 72 can be a passive resonant circuit tuned to the frequency of the pulses which amplifies the signal between the electrodes, or a simple first order high pass filter made by an RC circuit, the values of R and C being chosen so as to greatly reduce the physiological signals compared the hysteresis of comparator 76. The physiological signals to be filtered out are essentially made up of myopotentials of the body and of depolarization waves (EGM signals) that propagate through the myocardium, whether spontaneous or stimulated. For example, a passive first order high pass filter with a cut-off frequency of 1 MHz attenuates of 80 dB the EGM signals whose spectral content is in the band 0-100 Hz, so that an EGM signal of 40 mV does not contribute more than 4 µV to the received signal collected on the electrodes 22' and 24' signal, which is generally of an amplitude of several tens of millivolts.

Amplitude detector 74 is preferably a peak-to-peak detector, configured as a rectifier consisting of two capacitors and two diodes. The voltage at the output of the detector 74 is equal to $V_{max}-V_{min}-2V_d$, where $V_{max}$ is the maximum of the received signal, $V_{min}$ is the minimum of the received signal after filtering, and $V_d$ is the threshold voltage of the diodes. If this threshold voltage is low, a well known state of the art peak-to-peak detector without losses can be achieved under the name of "active diode" which is implemented using several MOSFET switches in order to avoid the classical voltage drop in diodes.

The threshold $V_s$ of the comparator 76 is preferably set to $V_s=0V$ (the comparison level to 0 V simplifies the electronics associated with the circuit, compared to a comparator with a preset voltage). The hysteresis value depends on the noise level of reception. In the case of the example mentioned above (wake-up pulse generated at a voltage of ±1.5 V, with 40 dB attenuation) for a peak-to-peak voltage of 30 mV available at the output of the detector 74, the hysteresis of comparator 76 can be set, for example, to a value of about 15 mV.

Another spurious signal to be eliminated is that formed by an electrical stimulation pulse applied to the heart, which has a high amplitude that may inappropriately trigger wake-up circuit 66. To prevent this untimely triggering, an additional criterion can be added to validate the wake-up and generate the signal $S_w$. This condition is to check (stage 78) that the width t of the logic signal generated at the output of comparator 76 is below a predetermined duration T, When T is selected to be close to the duration of the wake-up signal pulse (which, in practice, is much shorter than a stimulation pulse).

To test this condition, a first solution is to count the time between the falling edge and rising edge of the received pulse 68', using a counter (e.g., a clock) preferably already available in the receiver device, provided that the cycle of the counter is shorter than the duration of the wake-up signal pulse. If after a certain time limit (time-out falling edge does not occur, the detection is disabled and the $S_w$ signal is not generated.

An alternative technique that may be used for validation of wake-up signal is to integrate the output signal of comparator 76, for example, using a simple RC circuit, and comparing the result to a predetermined threshold.

In either case, some time has to pass (the time-out delay) to discriminate a wake-up signal (short pulse) from a stimulation pulse (long pulse). In practice, a timeout delay period of about three to four times the duration of the wake-up signal pulse 68 is considered to be an acceptable compromise, which does not reduce too much the responsiveness of the wake-up circuit. Of course, other periods can be used.

The signal $S_w$ produced by wake-up circuit 66 starts the supply of power to the various active circuits of the receiver device, which can then receive and process for analysis the HBC signals. To reflect the start time of these receiver circuits to their power on, there is a latency $T_w$ (FIG. 5a) between the wake-up signal pulse 68 and pulse of the HBC signals 70 corresponding to the information to be transmitted.

Furthermore, if the channel quality is good enough to detect HBC signals of low amplitude without amplification, filtering stage 72, detection stage 74 and comparator stage 76 of the wake-up circuit 66 can also be used for HBC signal exchange. This reduces the complexity and size of the receiver device, using a single circuit for the wake-up of the receiver and the HBC data signal collection.

Thus wake-up circuit 66 in accordance with the present invention requires little energy because the stages 72 and 74 are made with purely passive circuits. The only power consuming element is the comparator 76, but the current CMOS technologies can allow achieving a continuously active hysteresis comparator with an extremely low average power consumption, on the order of tens or hundreds of nanowatts. By comparison, an active signal amplifier uses about 1000 times more power. This amount is negligible compared to the overall energy balance of a leadless capsule in its operational state with all its circuits active, which is around 5 to 10 µW.

With reference to FIGS. 7 and 8, a second implementation of the present invention will be described, which is particularly suitable for situations in which the first implementation is not suitable, such as cases of high attenuation (where high attenuation means up to ×1000, 60 dB) and/or of significantly degraded signal/noise ratio.

In this embodiment, the proposed wake-up signal is, as shown in FIG. 7, formed from pulse bursts such as 80 or 82, which encode one bit of binary signal, respectively '0' or '1'. This is an amplitude shift key ("ASK") type of amplitude modulation, an "all or nothing", the pulses being biphasic signals of constant amplitude A (peak to peak). For a basic pulse of duration $T_s$, a binary zero is encoded by a biphasic burst of n pulses, for example n=3 pulses as shown in FIG. 7, followed by a null signal for the same period $n*T_s$. The binary '1' are encoded by a burst of 2n biphasic pulses 82 (n=6 pulses in the illustrated example), followed by a null signal for $2n*T_s$.

This modulation is in fact a double modulation: in the baseband, the modulation is a pulse width modulation (PWM) in which the length of zeros is equal to $T_0$ (n pulses, then no signal, the duration of which is $n*T_s$) and the length of each is equal to $T_1=2T_0$. The amplitude of the resulting signal (illustrated at the top of FIG. 7) is then modulated in the baseband by a pattern of pulse bursts to get the two bursts 80 or 82 (illustrated at bottom of FIG. 7).

FIG. 8 shows a preferred embodiment of a wake-up circuit 68 to detect and discriminate these pulse bursts. This circuit includes first an envelope detector stage 84, advantageously comprising a voltage multiplier 86, followed by a rectifier and a passive low-pass filter 88, e.g., a first order low pass filter RC. In the example shown in FIG. 8, a multiplier-by-four circuit realized with capacitors and low threshold diodes is shown, such circuit being feasible in standard CMOS technology. This multiplier has the effect of storing at the output capacitor (capacitor of stage 88) terminals a voltage equal to four times the amplitude of the received signal on the electrodes 22' and 24', thus achieving an amplification of passive voltage (the fact of having an AC signal—the pulse burst—makes it possible to achieve such amplification without energy consumption).

With reference to FIG. 9, a representative demodulated signal $S_d$, obtained at the output of the envelope detector 84, relative to the representative very noisy input signal $S_i$, collected on the electrodes 22' and 24', are shown.

If the signal from the envelope detector 84 is applied to a decoder circuit 90 including, as in the first embodiment, a hysteresis comparator 92 receiving at one of its inputs the signal $S_d$, the reference voltage applied to other input is advantageously constituted by a dynamic threshold that is the average value of the signal $S_d$, obtained by an RC integrator circuit 94. This prevents the setting of the decoder circuit 90 according to the quality of the transmission channel (attenuation and signal/noise ratio). In other words, instead of a pulse of high amplitude as in the first embodiment, in this second embodiment multiple pulses of uniform amplitude are sent, and integration of the succession of these pulses is applied to achieve a comparable result.

The decoding of the detected signal is made with no clock, asynchronously, by storing the successive bits received and decoded in an N bit (predefined size) shift register 96. At the end of the reception of the sequence of bits, the content of the shift register is compared by a comparator 98 to a numerical reference code, stored in a register 100 of the device. If it matches, the signal $S_w$ is generated to wake-up the active circuits of the receiver device in the same manner as described for the first embodiment. Unlike the first embodiment, however, in this second embodiment there is no need to discriminate a communication pulse from a stimulation pulse as it is impossible to obtain the reference numerical value of the register 100 for a stimulation pulse.

The numerical value stored in the memory 100 may be a generic wake-up code (e.g., for an undifferentiated wake-up of all the devices in the system), or a code specific to each device acting as a receiver, so that the master transmitter device can selectively awake and communicate with a particular slave device of the system.

In this second embodiment, the detection quality of the wake-up signal depends on the duration of a bit and not just of the signal/noise ratio. The number of pulses encoding a bit (n bits to encode a '0' and 2n bits to encode a '1') can thus be increased and increases with the time constant (integration time) of the envelope detector to increase the quality of reception—with a corresponding reduction in the communication flow.

Again, the circuits of the wake-up circuit of the second embodiment are passive circuits, with the exception of the comparators 92 and 98, whose energy consumption is, however, extremely low, as explained above in connection with the first embodiment.

One skilled in the art will appreciate the present invention may be practiced by embodiments other than those disclosed herein, which are provided for purposes of illustration and not of limitation.

The invention claimed is:

1. A system for wireless communication between at least two active medical devices in which at least one active medical device is a transmitter device and at least one active implantable medical device is a receiver device, wherein:

the transmitter device comprises a first pair of electrodes and a transmitter means for generating a modulated pulse train comprising a wake-up plurality of pulses in a series corresponding to a communication to the receiver device, and a wake-up signal preceding said modulated pulse train, said wake-up signal having a predetermined characteristic pulse pattern, and for applying said wake-up signal and modulated pulse train to said first pair of electrodes; and the receiver device comprises an energy source, at least one active circuit element, a second pair of electrodes, and a receiver means for collecting a received signal at said first pair of electrodes and processing said received signal to identify therein a received wake-up signal and modulated pulse train corresponding to said wake-up signal and modulated pulse train from said transmitter means, and means for demodulating said received modulated pulse train into a received pulse train corresponding to said wake-up plurality of pulses;

wherein said receiver means further comprises means for selectively switching said at least one active circuit element between a sleep state not powered by said energy source and an operational state powered for processing said received signal using said at least one active circuit element; and, wake-up circuit means for discriminating said received wake-up signal having said predetermined characteristic pulse pattern, and in response, switching the receiver means from the sleep state to the operational state, wherein:

said wireless communication is an intracorporeal communication of electrical pulses conducted by the interstitial tissues of a patient's body; and the wake-up circuit means comprises a detector circuit and a hysteresis comparator.

2. The system of claim 1, wherein the wake-up circuit means has no active amplifier circuit.

3. The system of claim h wherein said wake-up signal comprises a biphasic pulse and said modulated pulse train further comprises a biphasic pulse train, each biphasic pulse having a positive alternation and a negative alternation.

4. The system of claim 1, wherein the wake-up circuit means has a permanent energy consumption of less than 10 nW.

5. The system of claim 1, wherein said predetermined characteristic pattern further comprises an initial pulse having a high amplitude corresponding to the wake-up signal, and wherein said following succession of pulses have lower amplitude than said high amplitude.

6. The system of claim 5, wherein the predetermined characteristic pattern further comprises a latency period between said initial pulse and the following succession of pulses.

7. The system of claim 5, wherein the receiver means further comprises one of a peak level detector and a peak-to-peak detector, of the received signal.

8. The system of claim 5, wherein the wake-up circuit means further comprises means for inhibiting the switching of the receiver means from the sleep state to the operational state upon detection of a received pulse having a width that is greater than an upper predetermined limit.

9. The system of claim 1, wherein the receiver means further comprising a predetermined value corresponding to an authorized wake-up signal, said predetermined characteristic pattern further comprises a first specific sequence of pulses of uniform amplitude encoding a predetermined binary value forming a wake-up code, and the wake-up circuit means comprises means for identifying the received signal and decoding therefrom a binary value encoded by said received signal first specific sequences of pulses, and comparing said decoded binary value with said predetermined value.

10. The system of claim 9, wherein the first specific sequence of pulses further comprises a plurality of distinct bursts of pulses, some of said bursts being a first number of pulses encoding a '1' bit and the other bursts being a second number of pulses, different from the first number, encoding a '0' bit, and wherein the receiver means further comprises an envelope detector delivering as output a series of binary values each obtained by integration of a received corresponding burst of pulses, and means for comparing said series of bits to said predetermined value.

11. The system of claim 10, wherein the envelope detector comprises a voltage multiplier circuit.

12. The system of claim 10, wherein the second number of pulses is double the first number of pulses.

13. The system of claim 1, wherein said modulated pulse train includes said wake-up signal preceding said plurality of pulses, and the means for demodulating said received signal further comprises means for demodulating said received modulated pulse train into a received pulse train corresponding to said wake-up signal and said wake-up plurality of pulses.

14. An autonomous active implantable medical device having wireless communications with a remote active medical device, having a receiver device comprising:
   an energy source;
   at least one active circuit element;
   a pair of electrodes;
   a receiver means for collecting a signal at said pair of electrodes and processing said received signal to identify therein a wake-up signal and a received modulated pulse train, said receiver means further comprising means for demodulating said received modulated pulse train into a received pulse train and identifying in said received pulse train a plurality of pulses;
   means for selectively switching said at least one active circuit element between a sleep state not powered by said energy source and an operational state powered for processing said signal using said at least one active circuit element; and,
   wake-up circuit means for discriminating said received signal and identifying therein a first signal having a predetermined characteristic pulse pattern and corresponding to a stored wake-up value, and in response, switching the receiver means from the sleep state to the operational state, wherein:
      said signal further comprises an intracorporeal communication of electrical pulses conducted by the interstitial tissues of a patient's body; and
      the wake-up circuit means further comprises a detector circuit and a hysteresis comparator.

15. The device of claim 14, wherein the wake-up circuit means has no active amplifier circuit.

16. The device of claim 14, wherein said wake-up signal further comprises a biphasic pulse and said modulated pulse train further comprises a biphasic pulse train, each biphasic pulse having a positive alternation and a negative alternation.

17. The device of claim 14, wherein the wake-up circuit means has a permanent energy consumption of less than 10 nW.

18. The device of claim 14, wherein said predetermined characteristic pattern further comprises an initial pulse having a high amplitude corresponding to the wake-up signal, and wherein said following succession of pulses have lower amplitude than said high amplitude.

19. The device of claim 18, wherein the predetermined characteristic pattern further comprises a latency period between said initial pulse and the following succession of pulses.

20. The device of claim 18, wherein the receiver means further comprises one of a peak level detector and a peak-to-peak detector, of the received signal.

21. The device of claim 18, wherein the wake-up circuit means further comprises means for inhibiting the switching of the receiver means from the sleep state to the operational state upon detection of a received pulse having a width that is greater than an upper predetermined limit.

22. The device of claim 14, wherein the receiver means further comprising a predetermined value corresponding to an authorized wake-up signal, said predetermined characteristic pattern further comprises a first specific sequence of pulses of uniform amplitude encoding a predetermined binary value forming a wake-up code, and the wake-up circuit means comprises means for identifying the received signal and decoding therefrom the first signal as a binary value encoded by said received signal first specific sequences of pulses, and comparing said decoded binary value with said predetermined value.

23. The device of claim 22, wherein the first specific sequence of pulses further comprises a plurality of distinct bursts of pulses, some of said bursts being a first number of pulses encoding a '1' bit and the other bursts being a second number of pulses, different from the first number, encoding a '0' bit, and wherein the receiver means further comprises an envelope detector delivering as output a series of binary values each obtained by integration of a received corresponding burst of pulses, and means for comparing said series of bits to said predetermined value.

24. The device of claim 23, wherein the envelope detector comprises a voltage multiplier circuit.

25. The device of claim 23, wherein the second number of pulses is double the first number of pulses.

26. The device of claim 14, wherein said modulated pulse train includes said wake-up pulse preceding said plurality of pulses, and the means for demodulating said received signal further comprises means for demodulating said received modulated pulse train into a received pulse train corresponding to said wake-up signal and said following plurality of pulses.

* * * * *